(12) United States Patent
Geist et al.

(10) Patent No.: US 12,016,606 B2
(45) Date of Patent: Jun. 25, 2024

(54) SURGICAL GUIDANCE DEVICE AND SYSTEM FOR INSERTION THEREOF

(71) Applicant: Integrity Implants Inc., Palm Beach Gardens, FL (US)

(72) Inventors: Wyatt Drake Geist, Davie, FL (US); Jared M White, West Palm Beach, FL (US)

(73) Assignee: INTEGRITY IMPLANTS INC., Palm Beach Gardens, FL (US)

(*) Notice: Subject to any disclaimer, the term of this patent is extended or adjusted under 35 U.S.C. 154(b) by 240 days.

(21) Appl. No.: 17/731,275

(22) Filed: Apr. 28, 2022

(65) Prior Publication Data

US 2022/0323133 A1 Oct. 13, 2022

Related U.S. Application Data

(62) Division of application No. 16/722,944, filed on Dec. 20, 2019, now Pat. No. 11,344,353.

(60) Provisional application No. 62/783,054, filed on Dec. 20, 2018.

(51) Int. Cl.
*A61B 17/88* (2006.01)
*A61B 17/17* (2006.01)
*A61B 17/70* (2006.01)
*A61B 17/86* (2006.01)

(52) U.S. Cl.
CPC ...... *A61B 17/8875* (2013.01); *A61B 17/1757* (2013.01); *A61B 17/7082* (2013.01); *A61B 17/864* (2013.01); *A61B 17/8897* (2013.01)

(58) Field of Classification Search
CPC .................................................. A61B 17/8875
See application file for complete search history.

(56) References Cited

U.S. PATENT DOCUMENTS

| 5,398,946 | A | * | 3/1995 | Quiring | ................ | B25D 17/088 |
| | | | | | | 403/325 |
| 8,715,293 | B2 | * | 5/2014 | Vandewalle | ....... | A61B 17/8875 |
| | | | | | | 606/86 R |
| 2007/0125201 | A1 | * | 6/2007 | Raines | .................... | B25B 21/00 |
| | | | | | | 81/429 |
| 2011/0054537 | A1 | | 3/2011 | Miller et al. | | |
| 2012/0004665 | A1 | | 1/2012 | Defossez et al. | | |

(Continued)

OTHER PUBLICATIONS

Anonymous, Alfa Tech, Retrieved from Internet Mar. 19, 2020, https://linkedin.com/posts/alfatec-spine_atec-organic-innovation-machine-activity-6628772455886528512-gm5n/.

(Continued)

*Primary Examiner* — Christian A Sevilla
(74) *Attorney, Agent, or Firm* — McHale & Slavin, P.A.

(57) ABSTRACT

Briefly, the invention relates to a surgical tool and method for forming a pilot bore by inserting a guide wire into bone. More particularly, the device includes a cannulated hand grip and driving tool used for the rotation of a pedicle screw into bone. The rear portion of the hand grip includes a slide assembly that is suited to grip a guide wire. The slide assembly includes a user adjustable stop to control the sliding movement of the guide wire. The rear surface of the slide assembly is constructed to be impacted with a hammer or similar device, whereby the stop prevents the guide wire from penetrating the bone further than desired. Should it be desired that the guide wire be retracted, a screw jack is included to allow the guide wire to be precisely retracted.

10 Claims, 11 Drawing Sheets

(56) References Cited

U.S. PATENT DOCUMENTS

2014/0094822 A1* 4/2014 Baynham ........... A61B 17/7002
  606/103
2016/0030100 A1* 2/2016 Divincenzo ........ A61B 17/7082
  606/104

OTHER PUBLICATIONS

Anonymous, Astura Spine, Retrieved from Internet Mar. 19, 2020, https://asturamedical.com/product/olympic-mis/.
Anonymous, Dupuy Spine, Retrieved from Internet Mar. 19, 2020, https://vimeo.com/260201759/.

* cited by examiner

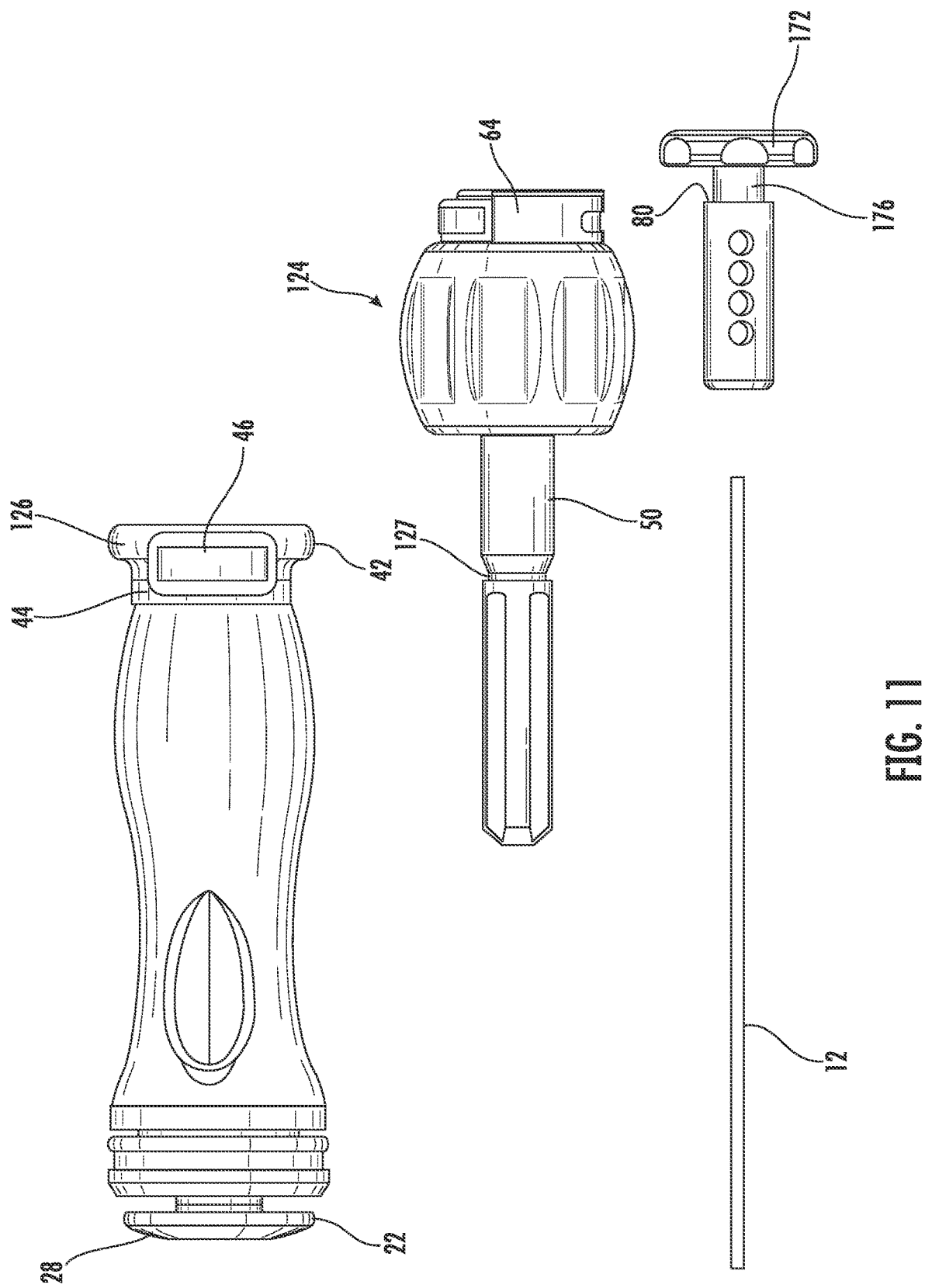

SURGICAL GUIDANCE DEVICE AND SYSTEM FOR INSERTION THEREOF

RELATED APPLICATIONS

In accordance with 37 C.F.R. 1.76, a claim of priority is included in an Application Data Sheet filed concurrently herewith. Accordingly, the present invention claims priority as a divisional to U.S. Non-Provisional patent application Ser. No. 16/722,944, entitled "SURGICAL GUIDANCE DEVICE AND SYSTEM FOR INSERTION THEREOF", filed on Dec. 20, 2019, which claimed priority to U.S. Provisional Patent Application No. 62/783,054, entitled "SURGICAL GUIDANCE DEVICE AND SYSTEM FOR INSERTION THEREOF", filed on Dec. 20, 2018. The contents of the above applications are incorporated herein by reference.

FIELD OF THE INVENTION

The invention relates to a guidance instrument and a device for insertion of the guidance instrument for surgical spinal procedures. In particular, the device includes a driving tool for inserting and positioning a guide wire into bone in addition to a tool for inserting a pedicle screw into a vertebra.

BACKGROUND

Medical procedures involving the vertebrae are normally complicated because of the preciseness and accuracy required to avoid both neural damage and injury to major blood vessels. Precision depth guided instruments are required to perform percutaneous spinal surgery. These surgeries sometimes require penetration of the hard cortical bone of the vertebra and traversal of the softer cancellous bone lying thereunder. A large force is normally required by the surgeon to penetrate the cortical bone. Once the cortical bone is penetrated, extreme care must then be taken to avoid rapidly penetrating through all of the cancellous bone. There is also the danger of rapidly passing through the cancellous bone and then through the cortical bone on the other side of the vertebra. This can result in injury or damage to the spinal cord and/or other organs or blood vessels located adjacent the spine. In some instances, the force required to penetrate the cortical bone is greater than a surgeon can apply by hand. In these instances, a hammer or other similar instrument is required to force the instrument through the cortical bone. When a hammer or similar instrument is used, there is a greater danger of the instrument passing rapidly through the cancellous bone and out the other side of the vertebra.

Thus, what is needed is a device and method for inserting a small diameter guide wire that is capable of precisely controlling the depth that the guide wire can penetrate. The device and method should also be constructed to allow the user to precisely retract the guide wire through bone as needed.

SUMMARY

Briefly, the invention relates to a surgical tool and method for forming a pilot bore by inserting a guide wire into bone. The surgical tool is constructed and arranged for use in conjunction with X-ray or ultrasound machines. More particularly, the device includes a cannulated hand grip and driving tool used for the rotation of a pedicle screw into bone. The rear portion of the hand grip includes a slide assembly that is suited to grip a guide wire. The slide assembly includes a user adjustable stop to control the sliding movement of the guide wire. The rear surface of the slide is constructed to be impacted with a hammer or similar device, whereby the stop prevents the guide wire from penetrating the bone further than desired. Should it be desired that the wire be retracted, a screw thread is included to allow the wire to be precisely retracted. The hand grip is securable to various surgical driving tools for the purpose of providing the ability to cooperate with various brands of pedicle screws and other surgical implants for spinal procedures. Thus, more than one driving tool may be secured to the same surgical tool, and the driving tool is rotatable about the longitudinal axis of the surgical tool. This construction saves the surgeon time by forming the pilot bore which may retain the guide wire. Since the pedicle screw is already positioned on the guide wire, the surgeon need only rotate the tool to insert the screw along the guide wire to its desired position. Once the screw is placed, the screw jack can be utilized to retract the guide wire.

Accordingly, it is an objective of the present invention to provide a surgical tool which can be utilized to provide a precise trajectory and insertion depth for a guide wire.

It is another objective of the present invention to provide a surgical tool for insertion of guide wires which can be secured to various drive tools for the insertion of a pedicle screw into a patient.

It is yet another objective of the present invention to provide a surgical tool for the insertion of a guide wire that includes a screw jack for retracting or removing a guide wire.

Still yet another objective of the present invention is to provide a surgical tool for formation of a pilot bore by insertion of a guide wire that includes a driving surface for a striking instrument and a stop for controlling the driving depth.

Still yet a further objective of the present invention is to provide a surgical tool that can be used to ensure a desired trajectory and/or depth of a pilot hole by advancing a guide wire or biopsy needle in any number of surgical procedures, such as bone marrow biopsies, placement of spinal implants, spinal surgery, including ensuring proper placement of pedicle screws during pedicle fixation procedures and ensuring proper trajectory during the establishment of an operative corridor to a target site.

Other objects and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 11 is an exploded view of the surgical tool illustrated in FIG. 8.

DETAILED DESCRIPTION

Figure 1:
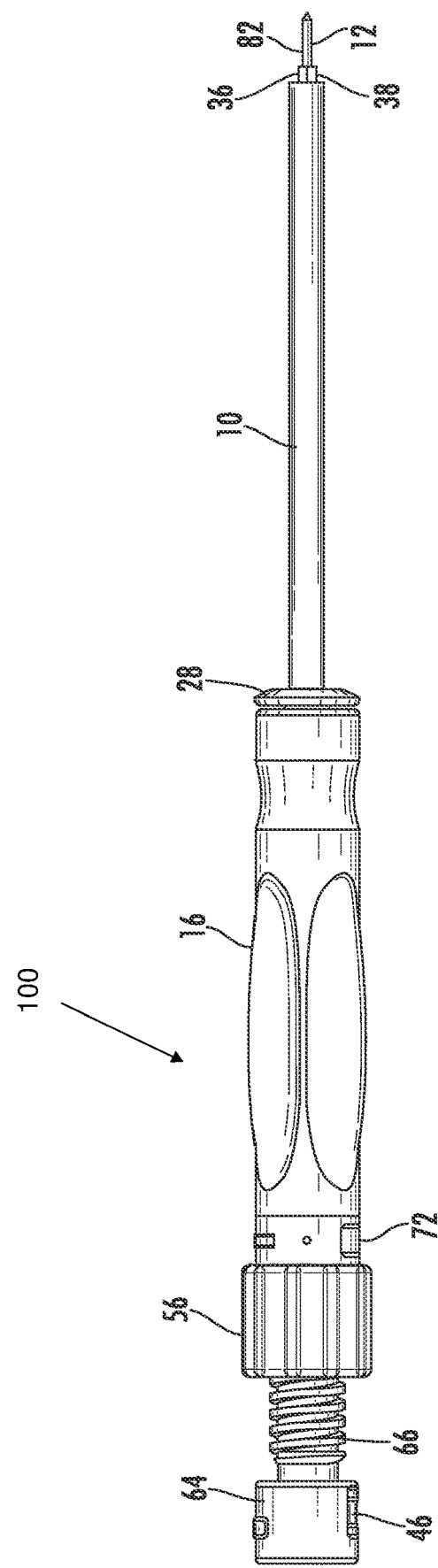
FIG. 1 is a side view of one embodiment of the surgical tool, illustrated with a guide wire and a driving tool for a pedicle screw.
Figure 2:
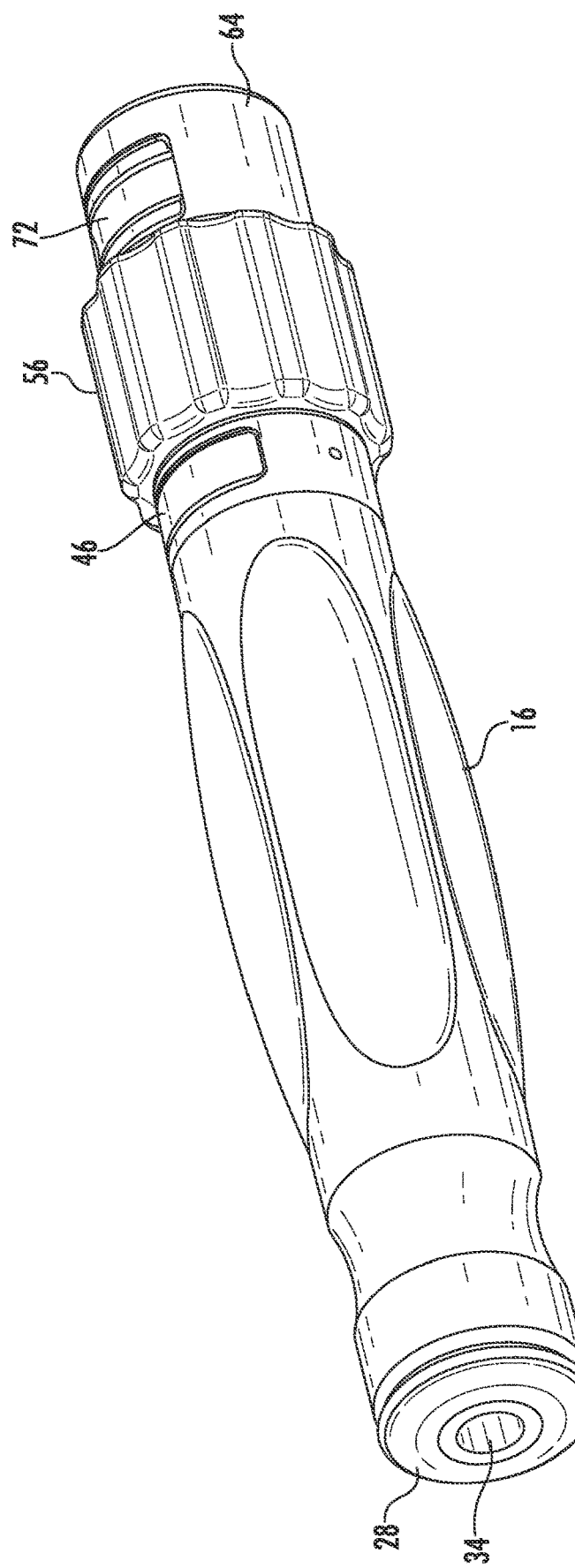
FIG. 2 is a perspective top view of one embodiment of the surgical tool.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Various embodiments and surgical uses of devices are described for enhancing the safety and efficiency of surgical procedures. In one example, set forth by way of example only, the present invention may facilitate safe and reproducible pedicle screw guidance and placement by controlling the axial trajectory of a guide wire for pilot hole formation and/or screw insertion. In another example, set forth by way of example only, intraoperative imaging performance may be improved and radiation exposure minimized by providing precise control to the surgeon during guide wire depth placement. In yet another example, controlling the trajectory and depth of surgical access instruments can aid in both the insertion and positioning of the access instruments themselves, as well as aiding in the later insertion of instruments and/or implants through or with the surgical access instruments. It is expressly noted that these examples are set forth by way of example, and that the present invention may be suitable for use in any number of additional surgical actions where the angular orientation, trajectory or depth (linear distance traveled) of instrumentation and/or implants is important. By way of example only, the present invention may be useful in directing, among other things, the formation of tunnels for ligament or tendon repair and the placement of facet screws. Another example would include bone biopsies and the like. Other uses may include orientation of drills, saws, cutters or other hand operated tools used in the performance of surgery where specific fiducial markers may be useful.

Figure 3:
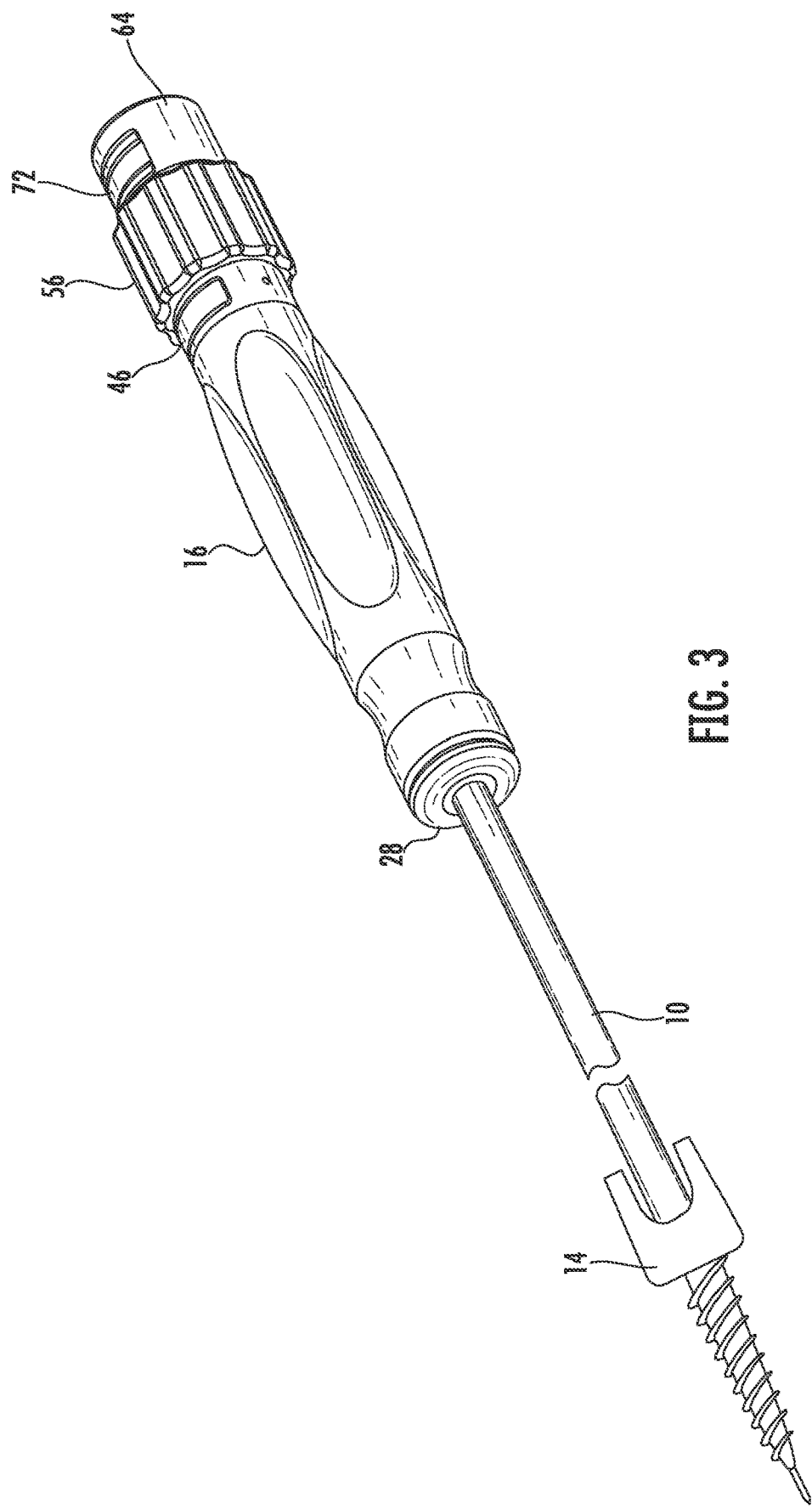
FIG. 3 is a top perspective view of the embodiment shown in FIG. 2, illustrated with a driving tool and pedicle screw.

FIGS. 1-8, which are now referenced, illustrate one embodiment of the present invention and one manner in which it may be assembled. Like reference numerals refer to like components in the various figures. FIGS. 1 and 3 illustrate a surgical tool 100 for operation of a driving tool 10, a guide wire 12 and a bone screw 14. By way of example only, while placing bone screws through a pedicle (which is a small generally tubular structure connecting posterior elements of a vertebra to the vertebral body), it is critical to ensure the bone screw is contained within the pedicle and does not breach the outer pedicle wall. Since the pedicle is surrounded by delicate nervous tissue, a breach can have serious consequences for the patient, ranging from mild pain to paralysis. One way to mitigate the risk of a pedicle breach during screw placement (including preparation for screw placement, such as pilot hole formation and tapping) is to determine the angular orientation of the pedicle, and thereafter advance the necessary instruments, guide wires and screws along the determined trajectory. By orienting the surgical access components along the pedicle trajectory with a guide wire, the surgical instruments and pedicle screws may be simply and efficiently advanced along the same trajectory, and thus avoid a breach.

Thus, in spinal surgery, before the pilot hole is formed with the guide wire 12, the desired angular trajectory must first be determined. Preoperative superior views utilizing AP fluoroscopy, MRI or CAT scan imaging device(s) are used to determine the trajectory once the surgical tool 100, in combination with the driving tool 10, pedicle screw 14 and guide wire 12, has been placed at the anatomical site for which the surgery is to be conducted. C-arm fluoroscopes are used extensively during many surgical procedures. During spinal surgery, for example, the C-arm is used frequently to help locate specific structures of the spine, to direct the positioning of surgical instruments and/or instrumentation, and to verify the proper alignment and height of vertebra, among other uses. Imaging devices, such as the C-arm, are typically provided with a scale (not shown) indicating the orientation of the radiography beam with respect to the patient and thus, in this example, the surgical tool 100 in combination with the driving tool 10, pedicle screw 14 and guide wire 12.

FIGS. 1-8, which are now referenced, illustrate one embodiment of the present invention and the manner in which it is constructed. In general, the figures illustrate a surgical tool 100 for creating a precise pilot bore using a guide wire 12 in a bone structure. The surgical tool 100 can further insert a bone screw 14 into the pilot bore without removal of the tool from the surgical site. The surgical tool 100 comprises a substantially rigid cannulated hand grip 16 including a first end 18 and a second end 20, the first end 18 including a quick release chuck 22 for securing to a driving tool 10, the second end 20 including a barrel 26 for housing a slide assembly 24. The hand grip 16 is secured to the barrel 26 in a manner that prevents rotation between the two. The hand grip 16 may be fixed to the barrel 26 by various means, which include overmolding, or can be detachably removable. In embodiments where the hand grip 16 is detachably removable, the hand grip 16 may include adhesive, keyways, press fits, serrations or the like which allow the hand grip 16 to adhere to the barrel 26 to prevent rotation between the hand grip 16 and the barrel 26 during operation. The quick release chuck 22 is operated by pressing the face plate 28 into the hand grip 16 depressing spring member 30 to allow the locking balls 32 to sufficiently retract to allow a driving tool 10 to be inserted or removed. Release of the face plate 28 allows the spring to force the face plate 28 outwardly, causing the locking balls 32 to retract inwardly to engage a ring or other indentions in the driving tool 10, preventing it from pulling out of the surgical tool 100. The quick release chuck 22 includes an inner sleeve 40 which includes the ramp surfaces for the locking balls 32. The inner sleeve 40 is also constructed to contain the spring member 30 while guiding the face plate 28. The inner surface 34 of the quick release chuck 22 and the driving tool 10 are provided with intermeshing, preferably conjugate shapes, which allow the surgical tool 100 to rotate the driving tool 10 in either direction. The distal end 36 of the driving tool 10 includes a shaped driver 38 which is constructed to cooperate with a female cavity in a bone screw 14 to allow the screw 14 to be rotated into a bone. The driving tool 10 includes a bore extending along the longitudinal axis of the driving tool 10 for passage of a guide wire 12, biopsy needle (not shown) or the like.

Figure 4:
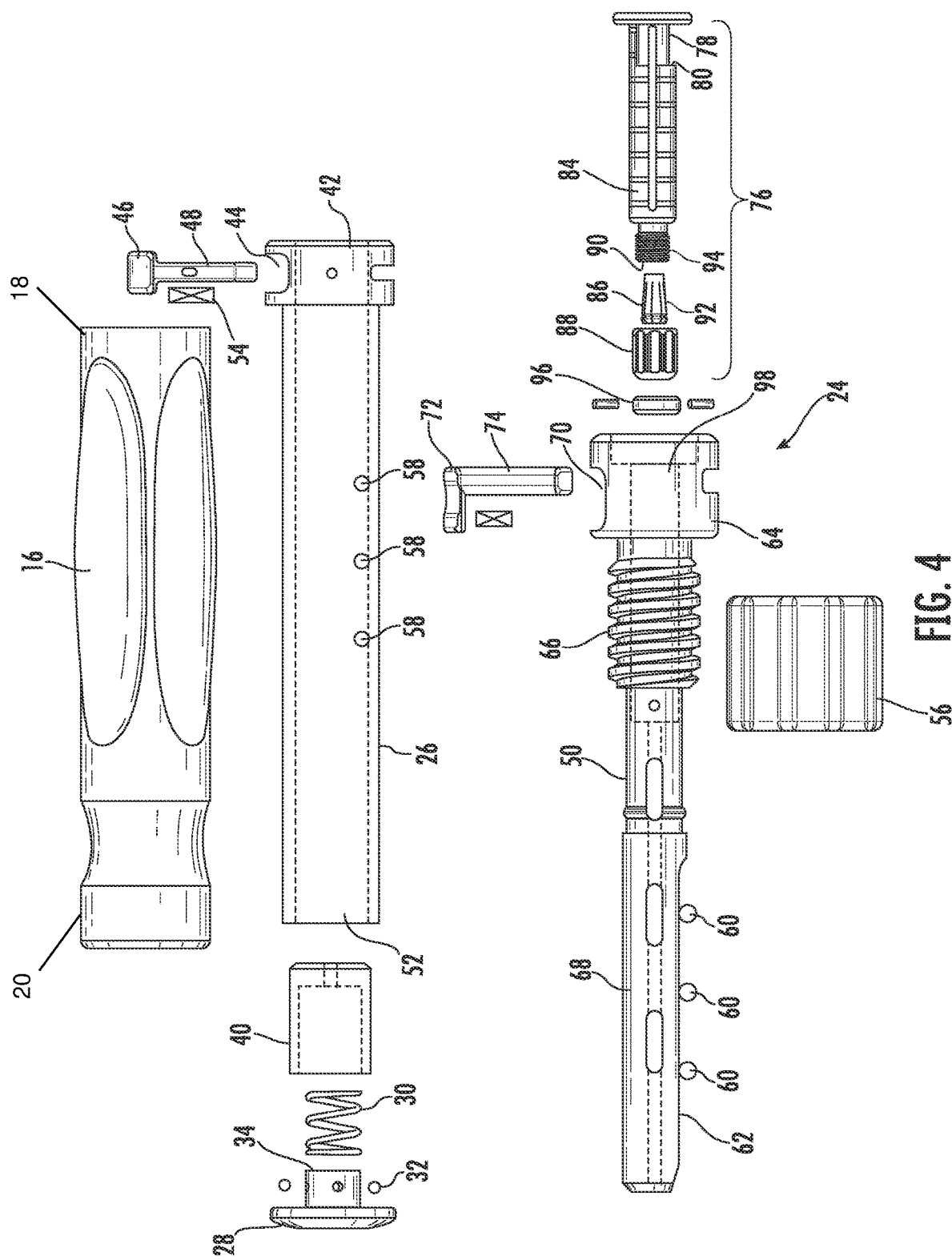
FIG. 4 is an exploded view of one embodiment of the surgical tool.

Referring to FIG. 4, barrel 26 is generally a tubular member having an enlarged head 42. The enlarged head 42 includes a slide lock bore 44 extending transversely across the barrel 26. The slide lock bore 44 is shaped to receive a slide lock 46. The slide lock 46 is spring loaded by a slide lock spring 54, and includes a bore 48 sized to accept and engage a side wall 50 of the slide assembly 24 to removably retain and position the slide assembly 24 within the bore 52 of the barrel 26. The slide lock 46 applies a predetermined pressure to the side wall 50, which allows the slide assembly 24 to move in a controllable manner within the barrel 26. Depression of the slide lock 46 allows the slide assembly 24 to be removed from and inserted into the barrel 26. Adjustment of the screw jack 56 provides a means to adjust and control the amount of travel provided to the slide assembly 24, which allows the guide wire to travel through the hand grip 16, barrel 26, and driving tool 10. The barrel 26 is also provided with tangent pin apertures 58, which cooperate with tangent pins 60 to prevent rotation of the slide assembly 24 during traversal of the slide assembly 24 within the barrel 26. The tangent pins 60 cooperate with tangent surface 62 to prevent the rotation.

Still referring to FIG. 4, the slide assembly 24 is generally constructed and arranged to control the travel of the guide wire 12 within the surgical tool assembly 100. The slide assembly 24 includes a slide head 64, threaded portion 66, side wall 50, wire guide portion 68 and tangent surface 62. The slide head 64 includes a transverse bore 70 sized and shaped to cooperate with a wire lock 72 having a bore 74 sized to cooperate with the outer surface of the wire chuck 76 to position and retain the wire chuck 76 within the slide assembly 24. Thus, a side surface of the wire lock bore 74 engages the lock surface 78, which includes a shoulder 80 to provide a positive stop. The slide assembly 24 is sized to fit within the barrel 26 for sliding movement between the two. The threaded portion 66 cooperates with the screw jack 56, which allows the amount of travel to be adjusted. The screw jack 56 also provides the ability to the surgeon to withdraw the guide wire 12 from bone and from a bone screw 14.

Figure 5:
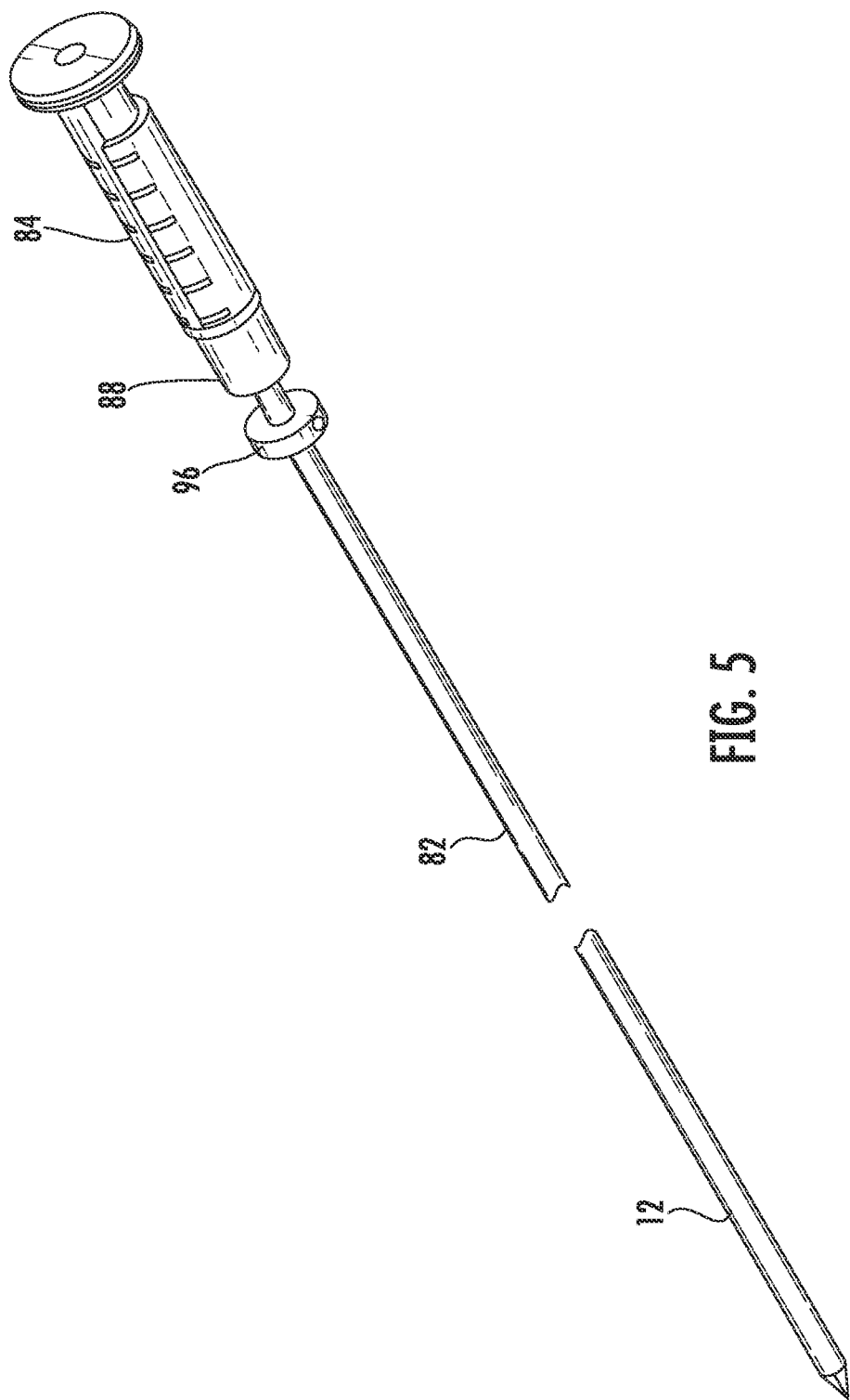
FIG. 5 is a perspective view of one embodiment of the guide wire chuck and anvil in cooperation with a guide wire.
Figure 6:
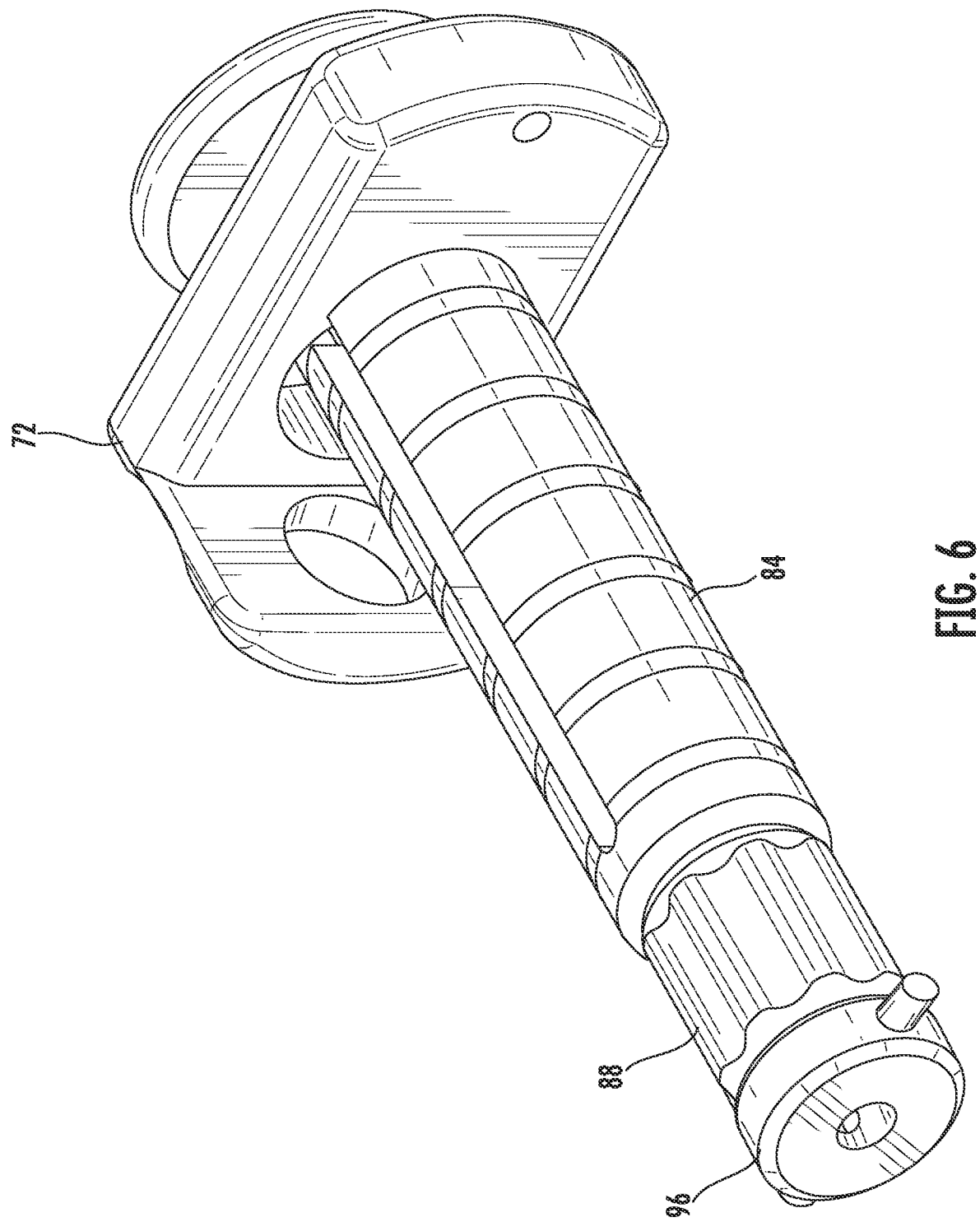
FIG. 6 is a perspective view of one embodiment of the guide wire chuck and anvil in cooperation with the wire lock.
Figure 7:
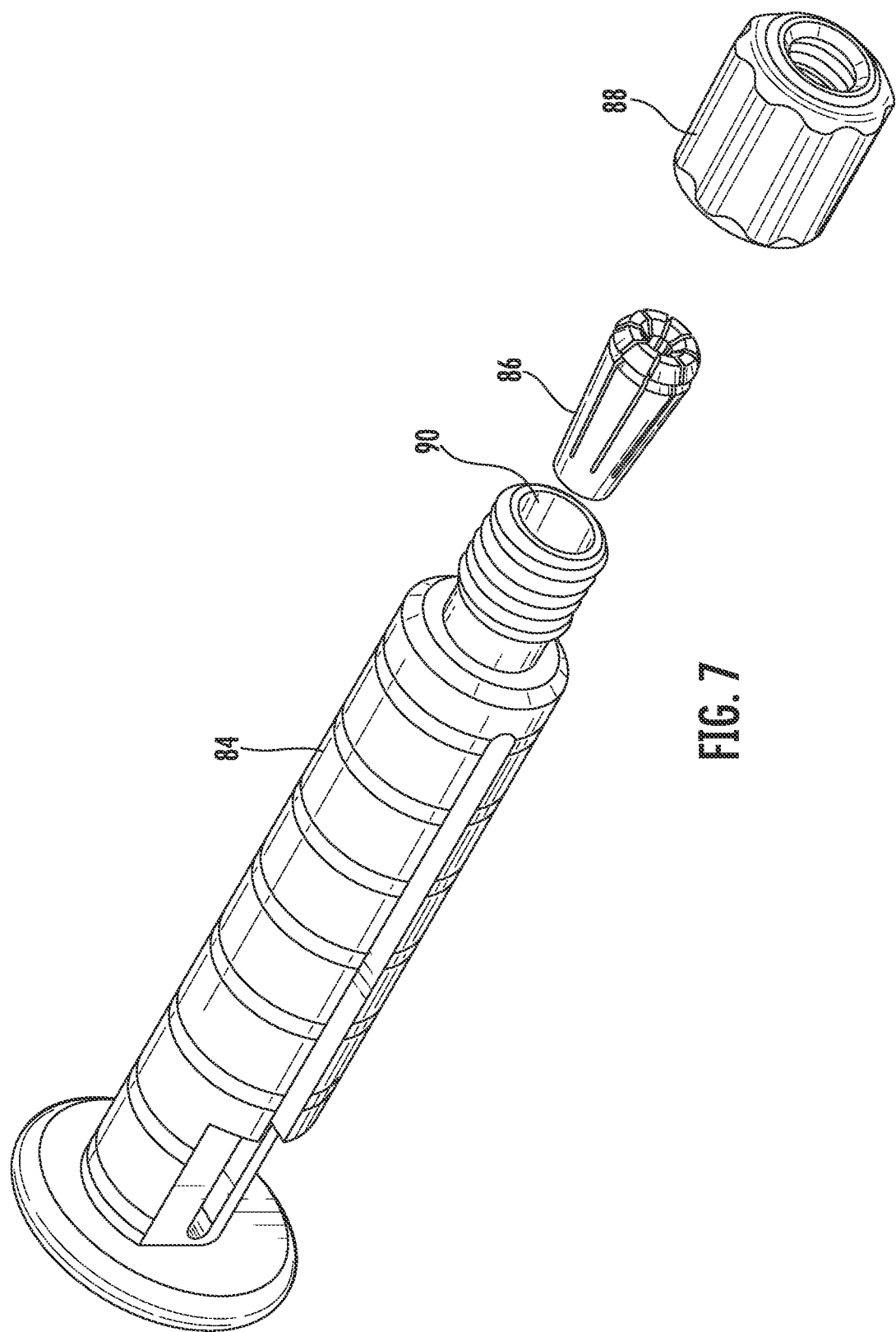
FIG. 7 is an exploded perspective view of the wire chuck assembly.
Figure 8:
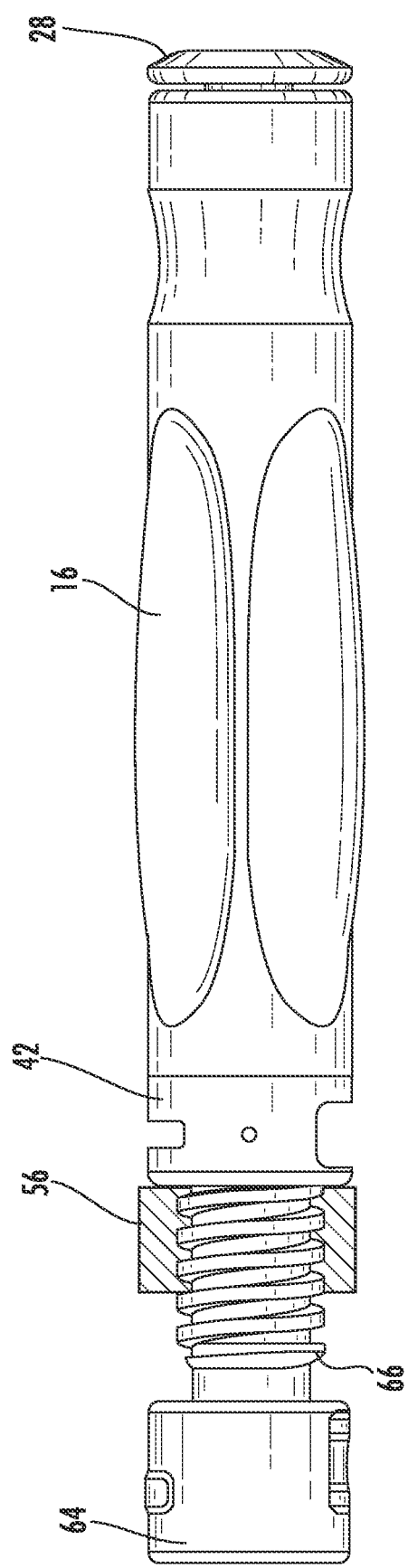
FIG. 8 is a partial view partially in section of the surgical tool, illustrating the cooperation between the slide and the screw jack.

Still referring to the figures, and particularly to FIGS. 4 and 5, the wire chuck 76 is generally constructed and arranged to engage a side surface 82 of the guide wire 12 to position the wire as desired by the surgeon. The wire chuck 76 includes the sleeve 84, collet 86 and collet closer 88. The sleeve 84 includes an internal taper 90 adapted to cooperate with the collet 86 when pushed into the sleeve 84 by the collet closer 88. In this manner, the movement of the collet closer 88 causes the internal taper 90 and the collet taper 92 to close the collet 86 on the outer surface of the guide wire 12 to position the guide wire. Threads 94 are provided on the outer surface of the sleeve 84, and an inner surface of the collet closer 88 to allow the user to precisely close the collet 86 to provide grip on the guide wire 12. An anvil 96 is provided and placed in bore 98 within the slide assembly 24. The anvil 96 provides a surface upon which the wire chuck 76 can impact without damage to the surgical tool assembly 100. It should be noted that while the collet 86 is illustrated as positioning the guide wire 12, the guide wire 12 may be provided with a head (not shown) that interlocks within the wire chuck 76 to position the guide wire 12. The guide wire 12 may be solid or cannulated, and may include any number of tips desirable for penetrating bone. It should also be noted that indicia may be included on the barrel 26, slide assembly 24, or screw jack 56 to assist the surgeon in controlling the movement of the guide wire 12. In some embodiments, the indicia may be embossed, printed, embedded or otherwise imprinted on a sticker or the like. In other embodiments, the indicia are etched or electro-plated into the hand grip 16. In some embodiments, the hand grip 16 may include a cutout region for accommodating indicia for depth.

One method of operation includes placing a bone screw 14 on the distal end 36 of driving tool 10. The guide wire 12 is secured in the wire chuck 76, having the approximate amount of guide wire extending outwardly therefrom. The guide wire 12 is slid through the slide assembly 24, depressing wire lock 72, allowing the wire chuck 76 to be locked into the slide assembly 24. The slide assembly 24 can then be inserted into the barrel and locked in place by depressing the slide lock 46, the guide wire 12 extending through the driving tool 10 and bone screw 14. Travel of the guide wire 12, and thus the amount that the guide wire 12 is allowed to extend through the bone screw 14, is adjusted by rotation of the screw jack 56. The guide wire 12 can then be retracted to not extend through the bone screw 14. The bone screw 14 can be positioned as desired on the bone, and the slide assembly 24 impacted with a hammer or the like to drive the guide wire 12 into position. The guide wire 12 may be retracted for insertion of the bone screw 14, or left in place while the screw is inserted into the bone. The screw jack 56 can be utilized to retract the guide wire 12 in either scenario.

Figure 9:
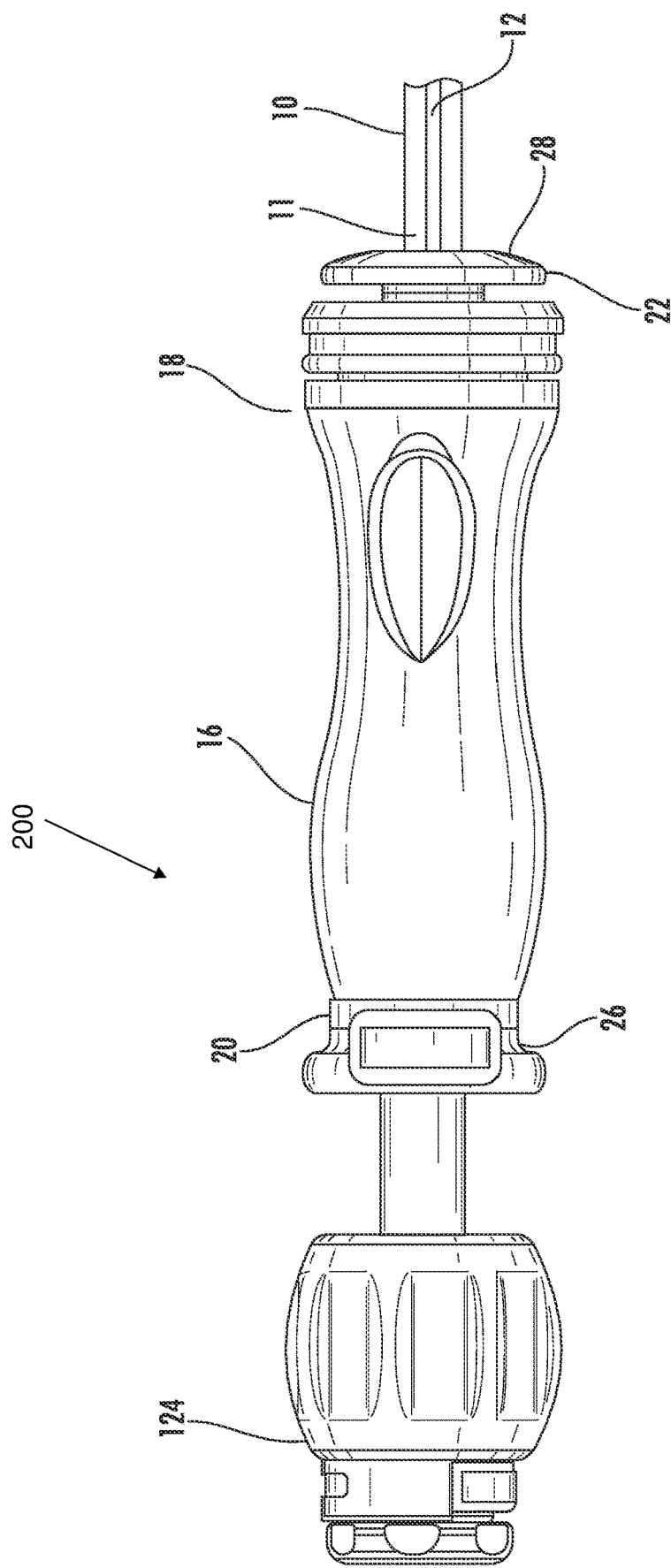
FIG. 9 is a side view of one embodiment of the surgical tool.
Figure 10:
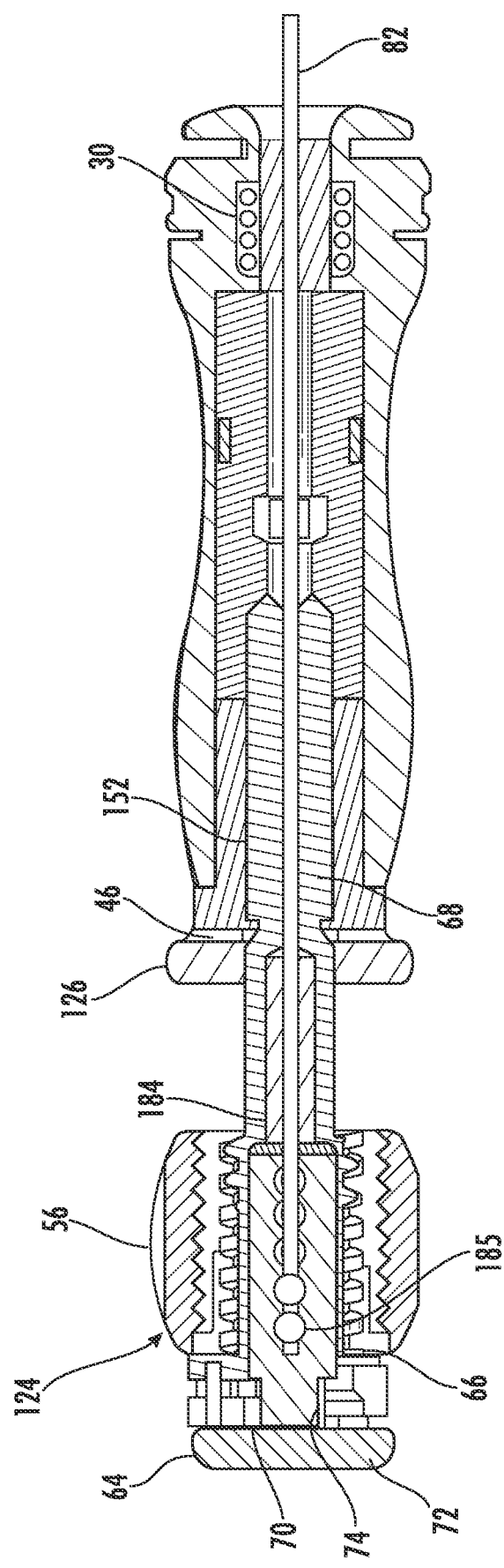
FIG. 10 is a section view taken along the longitudinal centerline of FIG. 8.

Referring to FIGS. 9-11, an alternative embodiment of the surgical tool 200 is illustrated. The surgical tool 200 comprises a substantially rigid cannulated hand grip 16 including a first end 18 and a second end 20, the first end 18 including a quick release chuck 22 for securing to a driving tool 10, the second end 20 including a barrel 26 for housing a slide assembly 124. The hand grip 16 is secured to the barrel 26 in a manner that prevents rotation between the two. The hand grip 16 may be fixed to the barrel 26 by various means, which include overmolding, or can be detachably removable. In embodiments where the hand grip 16 is detachably removable, the hand grip 16 may include adhesive, keyways, press fits, serrations, or the like, which allow the hand grip 16 to adhere to the barrel 26 to prevent rotation between the hand grip 16 and the barrel 26 during operation. The quick release chuck 22 is operated by pressing the face plate 28 into the hand grip 16, depressing spring member 30 to allow the locking balls 32 to sufficiently retract to allow a driving tool 10 to be inserted or removed. Release of the face plate 28 allows the spring member 30 to force the face plate 28 outwardly, causing the locking balls 32 (FIG. 4) to retract inwardly to engage a ring or other indentions in the driving tool 10, preventing it from pulling out of the surgical tool 200. The quick release chuck 22 includes an inner sleeve 40 (FIG. 4) which includes the ramp surfaces for the locking balls 32. The inner sleeve 40 is also constructed to contain the spring member 30 while guiding the face plate 28. The inner surface 34 of the quick release chuck 22 and the driving tool 10 are provided with intermeshing, preferably conjugate shapes, which allow the surgical tool 200 to rotate the driving tool 10 in either direction without slippage. The distal end 36 (FIG. 1) of the driving tool 10 includes a shaped driver 38 which is constructed to cooperate with a female cavity in a bone screw 14 to allow the screw 14 to be rotated into a bone. The driving tool 10 includes a bore 11 extending along the longitudinal axis of the driving tool 10 for passage of a guide wire 12, biopsy needle (not shown) or the like.

Referring to FIGS. 4 and 9-11, barrel 26 is generally a tubular member having an enlarged head 42. The enlarged head includes a slide lock bore 44 extending transversely across the barrel 126. The slide lock bore 44 is shaped to receive a slide lock 46. The slide lock 46 is spring loaded by slide lock spring 54 (FIG. 4), and includes a bore 48 sized to accept and engage a side wall 50 of the slide assembly 124 to removably retain and position the slide assembly 124 within the bore 152 of the barrel 126. The slide lock 46 applies a predetermined pressure to the side wall 50, which allows the slide assembly 124 to move in a controllable manner within the barrel 126. Annular groove 127 allows the slide assembly 124 to have a home position as illustrated in FIG. 9, from which mallet of the like can be used to advance the slide assembly 124 forward. Depression of the slide lock 46 allows the slide assembly 124 to be removed from and inserted into the barrel 126. Adjustment of the screw jack 56 provides a means to adjust and control the amount of travel provided to the slide assembly 124, which allows the guide wire 12 to travel through the hand grip 16, barrel 126, and driving tool 10. In this manner, the surgeon can control how far the guide wire 12 is allowed to travel into a bone, even when using a mallet or the like to advance the wire 12. The barrel 126 is devoid of pins, threads, or the like to allow rotation of the slide assembly 124 during traversal of the slide assembly 124 within the barrel 126. In this manner, the slide assembly 124 can be rotated or pulled in and out as desired. Alternatively, the annular groove 127 and the slide lock 45 can be used to retain the slide assembly 124 in a fixed position until it is desired to advance the guide wire 12 by hand or mallet.

Still referring to FIGS. 9-11, the slide assembly 124 is generally constructed and arranged to control the travel of the guide wire 12 within the surgical tool assembly 200. The slide assembly 124 includes slide head 64, threaded portion 66, side wall 50 and wire guide portion 68. The slide head 64 includes a transverse bore 70 sized and shaped to cooperate with a wire lock 172 having a bore 74 sized to cooperate with the outer surface 176 of the wire lock 172 to position and retain the wire lock 172 within the slide assembly 124. Thus, a side surface of the wire lock bore 74 engages the lock surface 176, which includes shoulder 80 to provide a positive stop. The slide assembly 124 is sized to fit within the barrel 126 for sliding and rotational movement between the two. The threaded portion 66 cooperates with the screw jack 56, which allows the amount of travel to be adjusted. The screw jack 56 also provides the ability to the surgeon to withdraw the guide wire 12 from bone and from a bone screw 14.

Still referring to FIGS. 9-11, the wire lock 177 is generally constructed and arranged to engage a side surface 82 of the guide wire 12 to position the wire 12 as desired by the surgeon. The wire lock 176 includes an inner bore 184, and a plurality of set screws 185 for engaging the side surface 82 to position the guide wire 12. It should be noted that while the bore and set screw(s) are illustrated as positioning the guide wire 12, the guide wire 12 may be provided with a head (not shown) that interlocks within the wire lock 176 to position the guide wire 12. The guide wire 12 may be solid or cannulated, and may include any number of tips desirable for penetrating bone, which may include split points such as those provided on drill bits. It should also be noted that indicia may be included on the barrel 126, slide assembly 124, or screw jack 56 to assist the surgeon in controlling the movement of the guide wire 12. In some embodiments, the indicia may be embossed, printed, embedded or otherwise imprinted on a sticker or the like. In other embodiments, the indicia are etched or electro-plated into the hand grip 16. In some embodiments, the hand grip 16 may include a cutout region for accommodating indicia for depth.

Another method of operation includes placing a bone screw 14 on the distal end 36 of driving tool 10. The guide wire 12 is secured in the wire lock 176, having the approximate amount of guide wire 12 extending outwardly therefrom. The guide wire 12 is slid through the slide assembly 124, depressing wire lock 72, 172, allowing the wire lock 176 to be locked into the slide assembly 124. The slide assembly 124 can then be inserted into the barrel 126 and locked in place by depressing the slide lock 46, the guide wire 12 extending through the driving tool 10 and bone screw 14. Travel of the guide wire 12, and thus the amount that the guide wire 12 is allowed to extend through the bone screw 14, is adjusted by rotation of the screw jack 56. The guide wire 12 can then be retracted to not extend through the bone screw 14. The bone screw 14 can be positioned as desired on the bone, and the slide assembly 124 impacted with a hammer, rotated with a drill, or the like, to drive the guide wire 12 into position. The guide wire 12 may be retracted for insertion of the bone screw 14, or left in place while the screw 12 is inserted into the bone. The screw jack 56 can be utilized to retract the guide wire 12 in either scenario.

It should be noted that, while not illustrated, the present device may be utilized for numerous orthopedic procedures that require precision and guidance. While not limited to the following list, such procedures may include other instruments such as drills, bone pins, hip, knee and shoulder replacements, as well as other surgical implantations where the surgeon desires to control the depth the tool is allowed to penetrate the bone. The device may also be applicable for biopsies of tissue, particularly for small tumors and the like where depth of the biopsy needle must be closely controlled. The present device may be used in parallel with devices, such as a drill, to control trajectory and depth of the drill.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical guidance device for inserting a guide wire and bone screw into a bone structure comprising:

a surgical tool having a cannulated hand grip, a driving tool, and a slide assembly; said cannulated hand grip including a first end and a second end, said first end including a quick release chuck for securing said hand grip to said driving tool, said second end including a tubular barrel for housing said slide assembly, said tubular barrel comprising a rear surface, said driving tool including a bore extending along a longitudinal axis of said driving tool for passage of a guide wire, a distal end of said driving tool including a shaped driver which is constructed to cooperate with a conjugately shaped portion of a bone screw to allow controlled rotation thereof, said tubular barrel positioned within said cannulated hand grip, said tubular barrel having a bore sized to slidably accept said slide assembly, said slide assembly having a slide lock, said slide lock extending transversely across said tubular barrel, said slide lock including a bore sized and shaped to receive said slide assembly, said slide lock including a slide lock spring to bias said slide lock to frictionally engage a side wall of said slide assembly to frictionally restrict forward and rearward movement thereof, said slide assembly including one or more annular groove(s), said annular grooves cooperating with the slide lock to provide the slide assembly with one or more fixed position(s), said slide assembly constructed and arranged for securement and positioning of said guide wire, the slide assembly comprising a front surface, said front surface of said slide assembly constructed to contact said rear surface of said tubular barrel for limiting forward travel of said slide assembly and said guide wire.

2. The surgical device of claim 1 wherein at least one of said annular grooves includes a ramping surface extending from a groove diameter to a slide assembly diameter, wherein a mallet can be used to advance said slide assembly over the ramping surface to advance the slide assembly.

3. The surgical device of claim 2 wherein said slide lock is constructed and arranged to be released from engagement with said slide assembly by hand.

4. The surgical device of claim 3 wherein said slide assembly includes a screw jack for limiting forward movement of said slide assembly with respect to said tubular barrel, said screw jack capable of contacting a portion of said tubular barrel to limit said movement.

5. The surgical device of claim 4, the surgical device comprising a wire chuck and a wire lock, wherein said slide assembly includes a slide head, said slide head includes at least one transverse bore sized and shaped to cooperate with said wire lock, said wire lock having a wire lock bore sized to cooperate with an outer surface of said wire chuck to position and retain said wire chuck within said slide assembly.

6. The surgical device of claim 5 wherein said wire chuck includes a shoulder to provide a positive stop to prevent longitudinal movement of said wire chuck without movement of said wire lock.

7. The surgical device of claim 6 wherein said wire lock is moveable by hand between a first position whereby said wire chuck is immovable longitudinally with respect to said slide head, and a second position whereby said wire chuck is moveable longitudinally with respect to said slide head.

8. The surgical device of claim 5 wherein said guide wire is a biopsy needle, said guide wire being cannulated.

9. The surgical device of claim 1 wherein said quick release chuck and said driving tool are provided with intermeshing shapes, which allow said surgical tool to rotate said driving tool in either direction rotationally.

10. A surgical guidance device for inserting a guide wire and bone screw into a bone structure comprising:

a surgical tool having a cannulated hand grip and a slide assembly, said slide assembly comprising a side wall and a front surface; said cannulated hand grip including a first end and a second end, said first end including a driving tool, said driving tool includes a shaped driver which is constructed to cooperate with a conjugately shaped portion of a bone screw to allow controlled rotation thereof, said second end including a tubular barrel for housing said slide assembly, said tubular barrel comprising a rear surface, said driving tool including a bore extending along a longitudinal axis of said driving tool for passage of a guide wire, said tubular barrel positioned within said cannulated hand grip, said tubular barrel having a bore sized to slidably accept said slide assembly, said slide assembly having a slide lock, said slide lock extending transversely across said tubular barrel, said slide lock including a bore sized and shaped to receive said slide assembly, said slide lock including a slide lock spring to bias said slide lock to frictionally engage said side wall of said slide assembly to frictionally restrict forward and rearward movement thereof, one or more annular groove(s) extending around the slide assembly cooperating with the slide lock to provide the slide assembly with one or more fixed stop position(s), said slide assembly constructed and arranged for securement and positioning of said guide wire, said front surface of said slide assembly constructed to contact said rear surface of said tubular barrel for limiting forward travel of said slide assembly and said guide wire.

* * * * *